US006436975B1

(12) United States Patent
Del Soldato

(10) Patent No.: US 6,436,975 B1
(45) Date of Patent: Aug. 20, 2002

(54) PHARMACEUTICAL COMPOSITIONS FOR ULCER

(75) Inventor: Piero Del Soldato, Milan (IT)

(73) Assignee: Nicox S.A., Paris (FR)

( * ) Notice: Subject to any disclaimer, the term of this patent is extended or adjusted under 35 U.S.C. 154(b) by 0 days.

(21) Appl. No.: 09/622,911

(22) PCT Filed: Feb. 25, 1999

(86) PCT No.: PCT/EP99/01225

§ 371 (c)(1),
(2), (4) Date: Aug. 29, 2000

(87) PCT Pub. No.: WO99/44595

PCT Pub. Date: Sep. 10, 1999

(30) Foreign Application Priority Data

Aug. 29, 2000 (IT) .......................................... MI98A0443

(51) Int. Cl.⁷ ............................................ A61K 31/425
(52) U.S. Cl. ...................... 514/365; 514/367; 514/925
(58) Field of Search ................................ 514/365, 367, 514/925

(56) References Cited

U.S. PATENT DOCUMENTS 5,700,947 A * 12/1997 Soldato ...................... 548/491

OTHER PUBLICATIONS

"New Guide to Medicine & Drugs", Brit. Medical Assoc. Editor, 1997, pp. 108–109.
"A Textbook of Drug Design and Development", Harwood Academic Publisher, 1991, p. 140.
"The Merck Index", Ed. 11th (1989).
"The Merck Index", Ed. 12th (1996).
Italian Patent Application No. MI97A 001440, 1997.
Radomski et al., Br. J. Pharmac., vol. 92, pp. 639–646 (1987); "The anti–aggregating properties of vascular endothelium: interactions between prostacyclin and nitric oxide".
"Remington's Pharmaceutical Sciences", Ed. 15th.
Robert et al., Gastroenterology vol. 77, pp. 433–443 (1979); "Cytoprotection by Prostaglandins in Rats".

* cited by examiner

*Primary Examiner*—Kevin E. Weddington
(74) *Attorney, Agent, or Firm*—Arent Fox Kintner Plotkin & Kahn

(57) ABSTRACT

Pharmaceutical compositions for the therapy and the prevention of ulcer and dyspepsia relapses comprising as essential components the following components a) and b): component a): one or more components selected from the conventional anti-ulcer products; component b): organic compounds containing the —$ONO_2$ function, or inorganic compounds containing the —NO group, characterized in that they are NO nitric oxide donors.

17 Claims, No Drawings

PHARMACEUTICAL COMPOSITIONS FOR ULCER

The Present invention relates to compositions to be used in the therapy and in the prevention of the ulcer relapses and, in general of the dyspepsias. More particularly it relates to compositions having an improved gastroprotectiie activity combined with an high acid secretion inhibition activity.

The products known in the art and those commercialized and used in the ulcer therapy are compounds which perform an anti-secretory activity (acid secretion inhibition). See for instance "New Guide to Medicine & Drugs" Brit. Medical Assoc. Editor, 1997, pages 108–109. Known products having higher therapeutic efficacy show an high anti-secretory activity and are used, both in the acute and in the longterm (6 months and more) therapies. The drawback of these products is that they have a poor gastroprotective activity, when present. From a practical point of view this means that the gastric protection is not optimal and causes inconveniences especially in the long-term therapy. In this case the presence of frequent relapses due to the enfeeblement of gastric mucosa is noticed.

To overcome these inconveniences it is known in the art to add to said medicaments other anti-ulcer medicaments having a gastroprocective action: prostaglandins, bismuth salts (e.g. bismuth citrate) and antibiotics. In such way the removal of ulcerous pathology is achieved. However these combinations are not sastisfactory as to their tolerability in general. For example it is well known that prostglandins produce side effects (diarrhoea) towards the intestinal tract; bismuth salts frequently produce nausea and heart-burn. Antibiotics produce undesired gastrointestinal effects.

The need was felt to have available compositions active in the ulcer and gastric dyspesia treatment having improved therapeutic characteristic and tolerability, general and local, in particular having an improved gastroprotective activity combined with an high anti-secretion activity.

The Applicant has unexpectedly and surprisingly found pharmaceutical anti-ulcer compositions having an improved therapeutic activity and tolerability.

It is an object of the present invention pharmaceutical compositions comprising as essential components the following: component a): one or more components selected from the following classes:

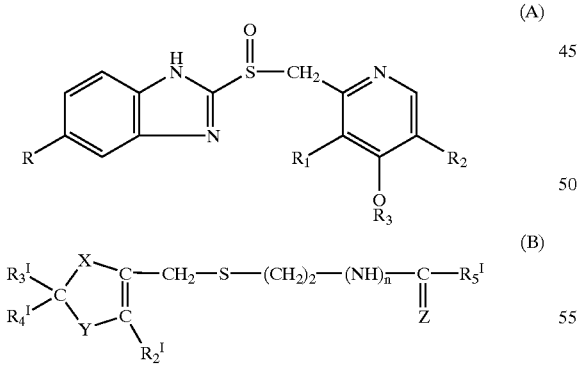

wherein in the (A) class compounds
R=H, $OCH_3$, $OCEF_2$;
$R_1$=$H_3$, $CH_3$;
$R_2$=CH, $CH_3$;
$R_3$=$CH_3$, $CH_2$—$CF_3$, $(CH_2)_3$—$OCH_3$;
wherein in the (B) class compounds:
$R'_3$, $R'_4$ equal to or different fromn each other, are respectively free valence, hydrogen, —N=====C $(NH_2)_2$, —$CH_2$—$N(CH_3)_2$;
Y=S, N—$R'_6$, $CR'_7R'_8$;
X=O, S, N—$R'_1$;
$R'_2$=H, $CH_3$;
n=0, 1;
Z=N—CN, N—$SO_2NH_2$, CH—$NO_2$ or (VII$_A$)

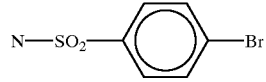

$R'_5$=H, —NH—$CH_3$, $NH_2$;
$R'_6$, $R'_7$, $R'_8$, $R'_1$, equal to or different from each other, are hydrogen, free valence;
component b): one or more organic compounds containing the —$ONO_2$ function, or one or more inorganic compounds containing the —NO group, or mixtures thereof, said compounds being characterized in that they are NO nitric oxide donors, i.e. when they are brought into contact in vitro with cells of the vasal endothelium, platelets, etc., and after incubation of 5 minutes at a temperature of 37° C., are capable to release NO and to activate the cGMP synthesis (Guanosine cyclic 3',5'-(hydrogen phosphate)), as shown by the used specific tests which will be described in detail further on.

The present invention compositions are obtainable by directly mixing the components a) and b).

The molar ratio between the components a) and b) can vary within wide limits, from 1:0.1 to 1:5, preferably from 1:0.5 to 1:2.

As regards the component a), the preferred (A) compounds are the following:
when R=$OCH_3$, $R_1$=$CH)_3$, $R_1$=$CH_3$, $R_3$=$_{CH3}$, Omeprazole residue;
as in Omeprazole, but with R=$OCHF_2$, $R_1$=$OCH_3$, $R_2$=H, Pantoprazole residue;
as in Omeprazole, but with R=H, $R_2$=H, $R_3$=$(CH_2)_3$—$OCH_3$, Rabeprazole residue;
as in Rabeprazole, but with $R_3$=$CH_2$—$CF_3$, Lansoprazole residue;
in component a) the preferred compounds of formula (B) are the following:
when in formula (B) X=N—$R'_1$ with $R'_1$ free valence, Y=N—$R'_6$ with $R'_6$=H, $R'_3$=H, $R'_4$ is free valence and forms with $R'_1$ a double bond, $R'_2$=$CH_3$, n=1, $R'_3$=—NH—$CH_3$, Z=N—CN, Cimetidine residue;
when X=N—$R'_1$ with $R'_1$ free valence, Y=S, $R'_3$=—N=$C(NH_2)_2$, $R'_4$ is free valence and forms with $R'_1$ a double bond, $R'_2$=H, n=1 $R'_5$=H, Z=(VII$_A$), Ebrotidine residue;
as in Ebrotidine but with n=0, $R'_5$=$NH_2$ and Z=N—$SO_2NH_2$, Famotidine residue;
as in Ebrotidine but with $R'_3$=—$CH_2$—$N(CH_3)_2$, $R'_5$=—NH—$CH_3$ and Z=CH—$NO_2$, Nizatidine residue;
as in Nizatidine, but with X=oxygen, Y=$CR'_7R'_8$ with $R'_7$ hydrogen and $R'_8$ free valence, $R'_4$ is a free valence and forms with $R'_9$ a double bond, Ranitidine residue.

In the preparation of the invention compositions also the isomers of one or more compounds of each component can be used.

The components belonging to (A) and (B) classes are prepared according to methods described in "The Merck Index 12$^a$ Ed."(1996), herein incorporated by reference.

In the formula (A) compounds of component a) also the compounds having the following intramolecular ring are comprised, obtainable by treating the precursors in an acid aqueous medium (ref. A Textbook of Drug Design and Development, Harwood academic publisher, 1991, pag. 140):

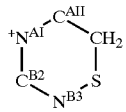

wherein $N^{AI}$ and $C^{AII}$ are, respectively, the nitrogen and the carbon atom in 1 and 2 position of the pyridine ring of formula (A) and $C^{B2}$ and $N^{B3}$ the carbon and nitrogen atom, respectively, in 2 and 3 position of the imydazole ring (1 position of the imydazole ring is that of the proton nitrogen).

Instead of the formula (A) and (B) compounds of component a) the corresponding salts with organic or inorganic salts, obtainable by reactions known to the skilled in the art, can be used. examples of usable inorganic ions are the following: hydrochlorides, nitrates, sulphates, phosphates, etc.; among the organic ones maleates, oxalates, acetates, succinates, etc. can be mentioned. Compositions containing nitrates are preferred.

The salts with the preferred compounds of the component a) are those corresponding to the preferred compounds of formula (A) or (B).

In the compositions according to the present invention salts of the compound of the above formulas contain at least one anion mole/compound mole. Preferably the ratio between the anion and compound moles is unitary. Salts having a higher molar ratio are obtained when in the molecule other basic enough aminic groups to be salif ied are present.

For example the salts of the class (A) and (B) compound with nitric acid are prepared according to the following methods.

When the substance to be salified is available as free base or as a corresponding salt soluble in an organic solvent, which preferably does not contain hydroxyl groups, for example acetonitrile, ethyl acetate, tetrahydrofuran, etc., the salt is prepared by dissolving the substance in the solvent at a concentration preferably equal or higher than 10% w/v, by adding the amount of concentrated nitric acid corresponding to the moles of salifiable aminic groups present in the compound. The nitric acid is preferably diluted in the same solvent. Preferably during and after the addition the mixture is cooled to temperatures in the range 20° C.–0° C. The product is generally recovered by filtration and washed with the solvent.

When on the contrary the substance is not very soluble, or it is available as a not very soluble salt in the above mentioned solvents, the corresponding mixtures with hydroxylated solvents may be used. Examples of such solvents are methyl alcohol, ethyl alcohol and water. Precipitation can be quickened by diluting then the so obtained mixture, after the addition of nitric acid, with an apolar solvent.

When the starting product is salified with hydrochloric acid, it is possible to prepare the nitric acid salt directly adding silver nitrate to the solution. After filtering silver chloride, the solution is concentrated and treated as above indicated to recover the nitrate salt.

When the starting product is a salt, it is also possible to liberate the corresponding base by a treatment with a sodium or potassium bicarbonate or carbonate saturated solution, or with a sodium or potassium hydroxide diluted solution. The base is then extracted by a suitable organic solvent (for example halogenated solvents, esters, ethers), which is then dried. The organic solution is evaporated and then one proceeds according to the preceding preparation methods, by dissolving the base in acetonitrile or in the other above mentioned solvents.

For the component b), the organic compounds containing the —$ONO_2$ groups which can be used are, as an example, the following, which are reported in The Merck Index 11th Ed-1989 and prepared by the known methods, for instance those mentioned in the same reference, herein incorporated by reference:

chlonitrate (3-chloro-1,2-propanediol dinitrate) (Merck No. 2390) having the formula $C_3H_5ClN_2O_6$ and structural formula

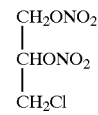

erythrityltetranitrate (1,2,3,4 butantetroltetranitrate) (Merck No. 3622) having the formula $C_4H_6N_4O_{12}$ and structural formula

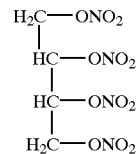

mannitol hexanitrate (Merck No. 5630) having the formula $C_5H_9N_6O_{18}$ and structural formula

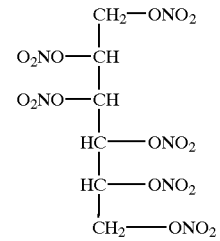

nicorandyl (N-[2-(nitroxy)ethyl]-3-pyridine-carboxamide) (Merck No. 6431) having the formula $CO_9H_9N_3O_4$ and structural formula

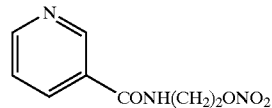

nitroglycerin (1,2,3 propanetriol trinitrate) (Merck No. 6528) having the formula $C_3H_5N_3O_9$ and structural formula

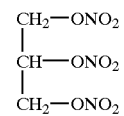

pentaerythritoltetranitrate (2,2-bis[(nitroxy)-methyl]-1,3-propanedioldinitrate) (Merck No. 7066) having the formula $C_5H_8N_4O_{12}$ and structural formula

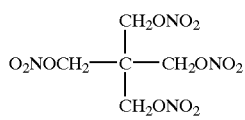

pentrinitrol (2,2-bis[(nitroxy)methyl]-1,3-propanediolmononitrate) Merck No. 7094) having the formula $C_{5H9}N_3O_{10}$ and structural formula

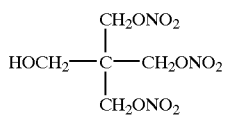

propatylnitrate (2-ethyl-2-[(nitroxy) methyl]-1,3-propanedioldinitrate) (Merck No. 7821) having the formula $C_5H_{11}N_3O_9$ and structural formula

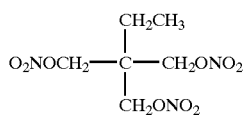

trolnitratephosphate (2,2',2''-nitryltrisethanoltrinitrate phosphate) (1:2 salt) (Merck No. 9682) having the formula $C_5E_{18}N_4O_{17}P_2$ and structural formula

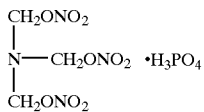

Other compounds containing the —$ONO_2$ group which can be used are prostglandin nitroderivatives described in the PCT/EP Application 98/03645 in the Applicant's name. This patent application is herein incorporated by reference both for compounds and preparation processes.

Among the inorganic compounds containing the —NO group can be mentioned:
  nitrate salts of alkaline, earth-alkaline or III group metals, for example with aluminum, sodium and potassium nitrates are preferred;
  nitroprussiate salts, such as for example: sodiumnitroprussiate (pentakis (cyano-C)nitrosylferrate(2-) disodium) (Merck No. 8600), having the formula $Na_2[Fe(CN)_5NO]$.

The invention components b) containing the —$ONO_2$ groups or the —NO group which produce the invention results, as already said, must meet the test in vitro described in detail hereinunder.

Specifically the test relates to the nitric oxide generation from the NO-donors described in the present invention, among which, for instance nitroglicerin, nicorandyl, nitroprussiate, etc., when they are put in the presence of endothelial cells (method a) or platelets (method b)

a) Endothelial Cells

Cells of the human umbilical vein, spread on plate, with a $10^3$ cells/plate density have been incubated with scalar concentrations of NO-donor (1–100 μg/ml) for 5 minutes. The incubation medium (physiologic solvent, for example Tyrode) has been then analyzed to determine the capability to generate NO, by:
  1) the nitric oxide disclosure by chemiluminiscence;
  2) cGMP determination (cyclic GMP No. 2715 of the above mentioned Merck).

As regards the chemiluminiscence analysis, an amount equivalent to 100 ul was injected in the reaction chamber of a chemiluminiscence analyzer containing glacial acetic acid and potassium iodide. Nitrites/nitrates present in the medium under these conditions are converted into NO which is then determined after its reaction with ozone, with consequent light generation. As it usually occurs in the devices measuring the chemiluminiscence, the produced luminiscence is directly proportional to the generated NO levels and can be measured by the suitable photomultiplier unit of a chemiluminiscence analyzer.

The photomultiplier converts the incident light into electric voltage, which is then quantitatively recorded. On the basis of a calibration curve, prepared with scalar nitrite concentrations, it was possible to quantitatively determine the generated NO concentration. For example, from the incubation of 100 μM of nicorandyl, an amount equal to about 10 μM of NO was generated.

As regards the CGMP determination, a portion of the incubation medium (equal to 100 μl) was centrifuged at 1000 revolutions per 20 seconds. The supernatant was discharged and the sediment treated with iced phosphate buffer (pH 7,4). The cGMP level produced were tested, by specific immuno-enzymatic reactants. From such experiments it resulted that, under these experimental conditions, the incubation with one of the various tested NO-donors caused a significant cGMP increase with respect to the values obtained in absence of a NO donor. For example, after incubation with 100 μM of sodium nitroprussiate, an increase of about 20 times the value obtained with the incubation of only the vehicle without NO donor was recorded.

b) Platelets

Washed human platelets, prepared analogously with what described by Radomski et al, (Br.J. Pharmacol. 92, 639–1987), were used. 0.4 ml alicuots were incubated with scalar NO-donor concentrations (1–100 μg/ml) for 5 minutes. The incubation medium (e.g. Tyrode) was then analyzed to determine the capability to generate NO, by determination of nitric oxide bv chemiluminiscence and CGMP, with the modalities described in the previous paragraph, for the analyses carried out on the endothelial cells. As to the determination by chemiluminiscence, also in this case, on the basis of a calibration curve, prepared with scalar nitrite concentrations, it was possible to quantitatively determine the generated NO concentration. For example, after incubation of 100 μM of nicorandyl, an amount equal to 35 μM of NO was generated.

As regards the cGMP determination, also in these experimental conditions it resulted that the incubation with one of the various NO-donors tested caused a cGMP significant increase with respect to the values obtained in absence of a NO-donor. For example, after incubation with 100 μM of sodium nitroprussiate, an increase of about 30 times the value obtained with the incubation of only the vehicle without NO-donor was recorded.

In conclusion, from said tests it results that all the NO-donors according to the present invention, after incubation with endothelial cells or platelets for 5 minutes, are capable to generate NO, and to activate the cGMP synthesis in a concencracion-depending way, as determined by the used specific tests.

It has now surprisingly been found that the present invention compositions allow to improve, compared with the known above mentioned combinations, the total pharmaco-toxicological behaviour of the compounds forming the component a), increasing the therapeutic efficacy and their general and local tolerability in the ulcer and gastric dyspepsia treatment, with improved gastroprotective activity.

The present invention compositions are formulated in the correspnding pharmaceutical compositions according to well known techniques in the field together with the conventional excipients; see for example the volume "Remington's Pharmaceutical Sciences 15a Ed."

The administering of the present invention compositions can be carried out by oral, parenteral or transdermic way. The component b) can generally be administered contemporaneously, subsequently or previously to the component a). The (A) and (B) compound doses of component a) are the conventional ones for these compounds.

It is a further object of the invention compositions obtainable by combining the pharmaceutical compositions according to the present invention with conventional gastroprotective agents. As examples, prostaglandins, bismuth salts, active antibiotics towards pathogenic microorganisms in the gastrointestinal mucosa can be mentioned.

It has surprisingly been found that the gastroprotective activity of the invention compositions is very high. This makes it possible to avoid the undesired effects of known gastroprotectives when they are used in combination with compounds or formulations of the invention compounds. It has indeed been found that the amount of the known gastroprotective agents, in the combination of the invention, is lower compared with those known and does not cause undesirable side effects. The skilled in the field is able to easily determine the maximum amount of conventional gastroprotective agents to be combined with the invention pharmaceutical compositions, since this corresponds to the absence of typical side effects of the known gastroprotective agents. In any case the amount of conventional gastoprotective agents to be used in the combination is lower than that used in combinations described in the art.

The following examples have the purpose to illluscrate the invention and must not be considered as limitative of the same.

EXAMPLE 1

Pharmaceutical composition.

Mixture formed by:

Component a) cimetidine 50 g.

componente b) KNO 20 g.

Amounts of this mixture corresponding to 70 mg/kg, or multiples, to be supplied to animals, are then weighed.

Pharmacological Tests

EXAMPLE 2

Acute Toxicity

To a group of 10 rats weighing 20 g each a single dose equal to 280 mg/kg of the Example 1 composition was supplied by oral way in a carboxymethylcellulose aqueous suspension 2% w/v.

The animals are kept under obsevation for 14 davs. In no one of the group animals the toxic syntom presence was noticed.

EXAMPLE 3

Anti-ulcer Activity

The anti-ulcer activity is evaluated according to the experimental model described in the paper of A. Robert et Al. "Cytoprotection by prostaglandins in rats. Prevention of gastric necrosis produced by alcohol, HCl, NaOH, hypertonic NaCl and thermal injury" Gastroenterology 77, 433–43 1979.

To 3 groups of 10 rats each, kept with empty stomach since the previous night, 15 minutes before the supply of absolute ethanol (1 ml), by oral way are supplied:

5 ml/Kg of carboxymethylcellulose aqueous suspension 2%.

50 mg/Kg of cimetidine in 5 ml/Kg of carboxymethylcellulose aqueous suspension 2%.

70 mg/Kg of the Example 1 composition in 5 ml/Kg of carboxymethylcellulose aqueous suspension 2%.

One hour later the animals are sacrificed and the gastric lesion incidence is evaluated. The results are reported in Table I and they show that the combination cimetidine and potassium nitrate shows an improved gastroprotective activity with respect to cimetidine.

TABLE I

| Treatment | Gastric Damage (%) |
|---|---|
| Vehicle | 100 |
| Cimetidine 50 mg/Kg | 100 |
| Composition Ex. 1 70 mg/Kg | 60 |

What is claimed is:

1. Pharmaceutical compositions comprising as components the following:

component a):

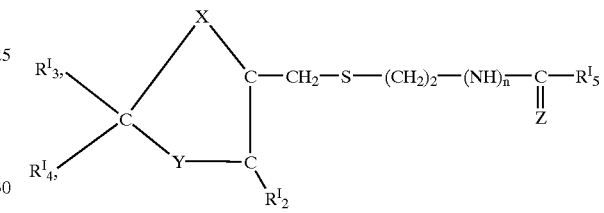

(B)

wherein:

$R^I_3$, $R^I_4$ equal to or different from each other, are respectively free valence, hydrogen,
—N=C(NH$_2$)$_2$, —CH$_2$—N(CH$_3$)$_2$;
Y=S, N—$R^I_6$, C$R^I_7R^I_8$;
X=O, S, N—$R^I_1$;
$R^I_2$=H, CH$_3$;
n=0, 1;
Z=N—CN, N—SO$_2$NH$_2$, CH—NO$_2$ or

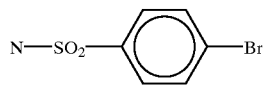

(VII$_A$)

$R^I_5$=H, —NH—CH$_3$, NH$_2$;
$R^I_6$, $R^I_7$, $R^I_8$, $R^I_1$, equal to or different from each other, are hydrogen, free valence;

component b): one or more organic compounds containing the —ONO$_2$ group, or one or more inorganic compounds containing the —NO group, or mixtures thereof, said compounds being characterized in that they are NO nitric oxide donors, i.e. when they are brought into contact in vitro with cells of the vassal endothelium, platelets, and after incubation of 5 minutes at a temperature of 37° C., are capable to release NO and to activate the cGMP synthesis (Guanosine cyclic 3',5'-(hydrogen phosphate)).

2. Pharmaceutical compositions according to claim 1, wherein the molar ratio between the components a) and b) varies from 1:0.1 to 1:5.

3. Pharmaceutical compositions according to claim 1 wherein in component a) the compounds are the following: formula (B):

X=N—R'$_1$ with R'$_1$ free valance, Y=N—R'$_6$ with R'$_6$=H, R'$_3$=H, R'$_4$ is free valence and forms with R'$_1$ a double bond, R'$_2$=CH$_3$, n=1, R'$_5$=—NH—CH$_3$, Z=N—CN, Cimetidine residue;

when in the formula (B) X=N—R'$_1$ with R'$_1$ free valence, Y=S, R'$_3$=—N=C(NH$_2$)$_2$, R'$_4$ is free valence and forms with R'$_1$ a double bond, R'$_2$=H, n=1 R'$_5$=H, Z=(VII$_A$), Ebrotidine residue;

as in Ebrotidine but with n=0, R'$_5$=NH$_2$ and Z=N—SO$_2$NH$_2$, Famotidine residue;

as in Ebrotidine but with R'$_3$=—CH$_2$—N(CH$_3$)$_2$, R'$_5$=—NH—CH$_3$ and Z=CH—NO$_2$, Nizatidine residue;

as in Nizatidine, but with X=oxygen, Y=CR'$_7$R'$_8$ with R'$_7$ hydrogen and R'$_8$ free valence, R'$_4$ is a free valence and forms with R'$_8$ a double bond, Ranitidine residue.

4. Pharmaceutical compositions according to claim 1, wherein the isomers of one or more compounds of each component are used.

5. Pharmaceutical compositions according to claim 1, wherein said pharmaceutical compositions comprise organic or inorganic salts of component a).

6. Pharmaceutical compositions according to claim 1, wherein said pharmaceutical compositions comprise nitrate salts of compounds of component a).

7. Pharmaceutical compositions according to claim 5, wherein the salts contain at least one anion mole/compound mole.

8. Pharmaceutical compositions according to claim 1, wherein the organic compounds containing the —ONO$_2$ groups usable in component b) are selected from the following ones:

clonitrate, erytrityltetranitrate, mannitol hexanitrate, nicorandyl, nitroglycerin, pentaerythiitoltetranitrate, pentrinitrol, propatylnitrate trolnitratephosphate, prostaglandin nitroderivatives.

9. Pharmaceutical compositions according to claim 1 wherein the inorganic compounds containing the —NO group of comonent b) are selected from the following: nitrate salts of alkaline, earth-alkaline or III group metals, and nitroprussiate salts.

10. Pharmaceutical comositions according to claim 9 wherein the nitrate salts are sodium and potassium nitrate.

11. Pharmaceutical cotmositions according to claim 1 formulated for the oral, parenteral, transdermic administering.

12. Pharmaceutical compositions according to claim 11 wherein the component b) is administered contemporaneously, subsequently or previously to component a).

13. Pharmaceutical compositions obtainable by combining the compositions according to claim 1 with conventional gastroprotective agents.

14. Pharmaceutical compositions according to claim 13 wherein the conventional gastroprotective agents are selected from prostaglandins, bismuth salts and antibiotics.

15. Pharmaceutical compositions according to claim 2, wherein the molar ratio between the components a) and b) varies from 1:0.5 to 1:2.

16. A method of treating a patient with ulcer or dyspepsia relapses, said method comprising administering a therapeutically effective amount of the pharmaceutical composition according to claim 1.

17. A method of treating a patient with ulcer or dyspepsia relapses, said method comprising administering a therapeutically effective amount of the pharmaceutical composition according to claim 13.

* * * * *

UNITED STATES PATENT AND TRADEMARK OFFICE
CERTIFICATE OF CORRECTION

PATENT NO.    : 6,436,975 B1
DATED         : August 20, 2002
INVENTOR(S)   : Del Soldato It is certified that error appears in the above-identified patent and that said Letters Patent is hereby corrected as shown below:

<u>Title page,</u>
Item [30], Foreign Application Priority Data, please change the date of the Foreign Application Priority Data from "Aug. 29, 2000" to -- March 5, 1998 --.

Signed and Sealed this

Twenty-sixth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,436,975 B1
DATED        : August 20, 2002
INVENTOR(S)  : Del Soldato It is certified that error appears in the above-identified patent and that said Letters Patent is hereby corrected as shown below:

Title page,
Item [56], References Cited, please add the following:
-- FOREIGN PATENT DOCUMENTS
WO     97 31654A     09/1997 --
OTHER PUBLICATIONS, please add:
-- "Implication of Nitric Oxide Synthase Activity in the Genesis of Water Immerstion-Stress Induced Gastric Lesions in Rats: the Protective Effects of FK-506, Aliment. Pharmacol. Ther., Hisanaga, et al., Vol. 10, 1996, pages 933-940.
"Effect of Pibutidine Hydrochloride on Nitric Oxide Production in Rat Gastric Mucosa", Comm Mol. Path. Pharmacol., Kiuchi et al., Vol. 100, No. 3, 1998, pages 273-281. --

Signed and Sealed this

Eighteenth Day of May, 2004

JON W. DUDAS
*Acting Director of the United States Patent and Trademark Office*